US006589573B2

(12) United States Patent
Unno et al.

(10) Patent No.: US 6,589,573 B2
(45) Date of Patent: Jul. 8, 2003

(54) XANTHINE OXIDASE INHIBITOR AND METHOD FOR PRODUCING THE SAME

(75) Inventors: Tomonori Unno, Shizuoka (JP); Iwao Sakane, Shizuoka (JP); Takami Kakuda, Shizuoka (JP)

(73) Assignee: Ito En, Ltd., Tokyo (JP)

( * ) Notice: Subject to any disclaimer, the term of this patent is extended or adjusted under 35 U.S.C. 154(b) by 0 days.

(21) Appl. No.: 10/013,351

(22) Filed: Dec. 13, 2001

(65) Prior Publication Data

US 2002/0051825 A1 May 2, 2002

Related U.S. Application Data

(62) Division of application No. 09/661,568, filed on Sep. 14, 2000, now abandoned.

(51) Int. Cl.[7] .................. A61K 35/78; A61K 31/34; A01N 43/02; A01N 43/16; A01N 43/08
(52) U.S. Cl. .................. 424/769; 514/449; 514/453; 514/461; 514/468; 514/732
(58) Field of Search .................. 435/88; 514/453, 514/449, 461, 468, 732; 424/725, 774, 769

(56) References Cited

PUBLICATIONS

Tomonori Unno et al, "On Xanthine Oxidase Inhibition Effects by Banaba Leaf Extracts", The 53rd The Japanese Society of Nutrition and Food Science Conference and Scientific Meeting. (May 28–30, 1999).

Primary Examiner—Christopher R. Tate
Assistant Examiner—Michele C. Flood
(74) Attorney, Agent, or Firm—Sughrue Mion, PLLC

(57) ABSTRACT

In order to provide a xanthine oxidase inhibitor having as an effective component an extract from highly safe plants, ten kinds of plant materials were compared for the xanthine oxidase inhibition activity, and in consequence *Lagerstroemia speciosa* (banaba) was found to have the strongest activity. In addition, it was found that the xanthine oxidase inhibition activity was present in an "crude extract" obtained by extracting banaba with hot water or the like, "resin adsorbed components" obtained by adsorbing the crude extract on a styrene-divinyl benzene synthetic resin or the like, and "organic solvent soluble components" obtained by the partition of the resin adsorbed component between water and an organic solvent. Among them, the "organic solvent soluble components" described above were purified with high performance liquid chromatography to obtain "ellagic acid," an "ellagic acid derivative," an "ellagic acid analog compound" and a "lignan," which were found to have a more superior xanthine oxidase inhibitor activity. The present invention provides a xanthine oxidase inhibitor having each of these extracted materials as an effective component.

15 Claims, 5 Drawing Sheets

XANTHINE OXIDASE INHIBITOR AND METHOD FOR PRODUCING THE SAME

This is a Divisional of application Ser. No. 09/661,568 filed Sep. 14, 2000, now abandoned, the disclosure of which is incorporated herein by reference.

BACKGROUND OF THE INVENTION

1. Field of the Invention

The present invention relates to a xanthine oxidase inhibitor having an effective component derived from plants.

2. Related Art Statement

Xanthine oxidase that is contained at a great amount in liver, small intestine mucous membrane, and milk of mammals produces uric acid via xanthine from hypoxanthine in the final step of the degradation pathway of purine compounds.

Increase in concentrations of blood uric acid causes various diseases such as gout as hyperuricemia, therefore, uric acid producing inhibitors, that is, the xanthine oxidase inhibitors are clinically administered in order to treat hyperuricemia. Development of physiologically active substances capable of repressing the activity of xanthine oxidase has been attracting attention.

Until now, a number of compounds have been reported which have a xanthine oxidase inhibiting effect. Many of such compounds, however, were synthesized by chemical procedures, and it could never be said that they were highly safety for human bodies. Recently, from a viewpoint of the safety for human bodies, there have been disclosed xanthine oxidase inhibitors derived from natural sources (Japanese Patent Laid-open Publications 1993-244963, 1997-202733, and others). However, they do not have a sufficient effect of inhibiting xanthine oxidase to a satisfactory extent.

SUMMARY OF THE INVENTION

An object of the present invention is to provide a xanthine oxidase inhibitor, which has as an effective component highly safe components derived from natural sources and a superior effect of inhibiting the xanthine oxidase activity.

The inventors have examined plants worthy of utilizing as a xanthine oxidase inhibitor as to plants which have been provided for food for many years and found safe for human bodies. In consequence, it has been found that extract of *Lagerstroemia speciosa*, a plant belonging to the genus Lagerstroemia in the family Lythraceae, exhibits a strong effect of inhibiting xanthine oxidase, which leads to achieving the present invention.

Accordingly, a xanthine oxidase inhibitor of the present invention is characterized by containing as an effective component extracted components from "*Lagerstroemia speciosa*" belonging to the genus Lagerstroemia.

This "*Lagerstroemia speciosa*" grows in tropical regions including, for example, the Philippines, and is called banaba. Its extracted liquid is taken daily as tea in the Philippines and others, therefore the safety for human bodies is assured.

DETAILED DESCRIPTION OF THE INVENTION

Figure 1:
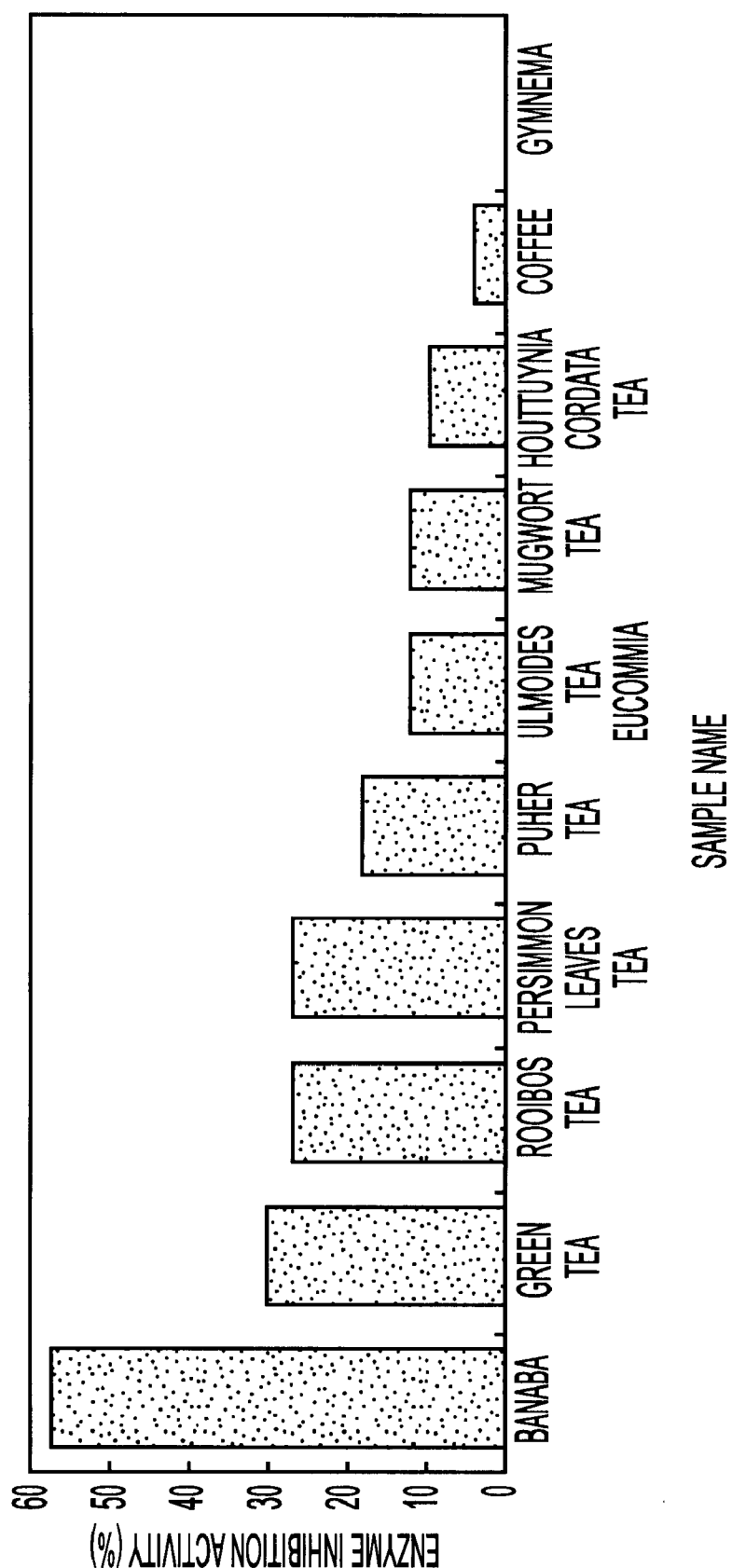
FIG. 1 is a graph showing the comparison of the xanthine oxidase inhibition activity of extracts obtained from ten plant materials with hot water.

As for parts of plant bodies which can be subjected to extraction in the present invention, every part such as leaves, stems, flowers, xylem, barks, roots, and the like is usable. Before the extraction, it is preferable that these plant parts are dried and milled for use.

As "extracted components" in the present invention, can be used a "crude extract" obtained by extracting the plant parts described above with water (including hot water), an organic solvent, or mixed solution thereof. The extraction temperature is preferably adjusted to the range of 40 to 100° C., particularly of 95 to 100° C.

As an organic solvent, it is preferable to use a water-soluble organic solvent like methanol, ethanol, and acetone. Optionally, combination of water and an organic solvent can be used according to needs.

When plant parts are extracted, it is preferable that the amount of hot water, an organic solvent, or a mixed solution of an organic solvent with hot water relative to the weight of the dried plant parts is 1:10 to 1:100, and in particular, 1:25.

As "extracted components", can also be used "resin adsorbed components" in the present invention, obtained by separation and purification of the above-mentioned "crude extract" by chromatographic techniques. In this case, "resin adsorbed components" can be obtained by adsorbing the above-mentioned "crude extract" onto a styrene-divinyl benzene synthetic resin (Diaion HP-10, 20, 30, 40, 50, produced by Mitsubishi Kasei Kogyou K.K.; Amberlite XAD-2, 4, produced by Organo Corp.; or Duolite S series, produced by Sumitomo Chemical Co., Ltd.), or a dextran synthetic resin (Sephadex LH-20, produced by Pharmacia; or the like), and then, by carrying out elution with an organic solvent, or optionally a mixed solution of water and an organic solvent. For example, "resin adsorbed components" can be collected by applying an "crude extract" to a column packed with Diaion HP-20, washing out non-adsorbed components with water, and eluting with methanol.

In addition, it is preferable that as "extracted components" in the present invention can be also used "organic solvent soluble components" obtained by partition of the above-described "resin adsorbed components" from water and an organic solvent such as chloroform, hexane, ethyl acetate, butanol, and the like.

Furthermore, as "extracted components" in the present invention can be also used "high performance liquid chromatography separated components" obtained by purification or isolation of the above-described "organic solvent soluble components" with high performance liquid chromatography.

The high performance liquid chromatography can be carried out on a column employing a separation mode such as a reverse phase, a normal phase, gel filtration, ion exchange, or hydrophobicentimeterode. From an economical viewpoint, it is preferable to carrying out it on a reverse phase mode. As one preferred example, a Diaion HP-20 resin adsorbed fraction can be subjected to partition with ethyl acetate and butanol to obtain an ethyl acetate soluble fraction and a butanol soluble fraction, respectively, and for the ethyl acetate soluble fraction, a reverse phase ODS column and 50 percent methanol (containing 1 percent acetic acid) as a eluting solution can be used to separate and collect the main components.

The "high performance liquid chromatography separated components" contain, as main components, ellagic acid, a derivative and analogue compound thereof, and a lignan, and each fraction of which has been found to have a superior effect of inhibiting xanthine oxidase. Therefore, any one or a mixture of two or more substances of ellagic acid, derivatives and analogue compounds thereof, and lignans obtained in this way can be also effectively used as "extracted components" in the present invention.

Methods for purifying the said ellagic acid, a derivative and analogue compound thereof and a lignan are not limited to the above-described method. If they are obtained from other plants, they can be used as an effective component of the xanthine oxidase inhibitor as well. In addition, combinations of extracted components obtained in each step described above can be also used.

Ellagic acid derivatives can include, in addition to valoneic acid dilactone described below, those which have an ellagic acid structure as the basic backbone and a sugar, lipid, amino acid, polyphenol, or the like bound to its hydroxyl groups, or in which its hydroxyl groups are substituted by or conjugated with methyl group, acetyl group, or the like. These will likely exert an effect similar to that of valoneic acid dilactone.

Ellagic acid analogue compounds are compounds having a similar structure to that of ellagic acid, such as 3,4,8,9,10-pentahydroxy-dibenzo[b,d]pyran-6-one, and for example, ellagitannin giving ellagic acid by hydrolysis, and the like. These will likely exert an effect similar to that of 3,4,8,9,10-pentahydroxy-dibenzo[b,d]pyran-6-one.

As obvious from examples below, banaba extracts which are a subject of the present invention have an effect of inhibiting the activity of xanthine oxidase, and can repress the production of uric acid. Such extracts, therefore, can be used to prevent and treat various diseases resulting from hyperuricemia, such as gout, and additionally manifest effects on prevention and treatment of various diseases resulting from active oxygen, such as inflammation, senescence, carcinogenesis, arterial sclerosis, brain disorders.

The xanthine oxidase inhibitors in the present invention can be provided for various applications as medicines, quasi drugs, cosmetics, foods, beverages (cans, PET bottles, bottles, and the like). They can be also provided as banaba tea beverages having a xanthine oxidase inhibiting effect.

In dosage forms, the xanthine oxidase inhibitor can be provided as powders by freeze drying, spray drying, or the like. Alternatively, it is possible to transform into solutions, tablets, granules, dragees, capsules, suspensions, emulsions, ampules, injections, and the like.

Although the above-described "extracted components" alone can be used as an effective component of the xanthine oxidase inhibitors, their effects can be further enhanced by using them in combination with other foods having a xanthine oxidase inhibiting effect, or alternatively allopurinol or alloxantin known as anti-hyperurocemia drugs, probenecid or benzbromarone known as uricosuric drugs, or the like.

DESCRIPTION OF THE PREFERRED EMBODIMENTS (Screening of Plant Materials)

Ten kinds of plant materials known as so-called health tea were collected to carry out comparison and examination of their effects of inhibiting the enzyme activity of xanthine oxidase.

Each plant material was ground with a mill, and a quantity of 0.5 g was placed into a screw-capped Erlenmeyer flask, followed by adding 50 ml of hot water, and extracted for 30 minutes. The resulting extract was passed through a filter to determine an effect of inhibiting the enzyme activity of xanthine oxidase, according to the measurement method described later. The results are shown in FIG. 1.

The results in FIG. 1 reveal that the component obtained by extracting banaba leaves (crude extract) is superior compared with other materials.

Next, a hot-water extract of banaba leaves (crude extract) was prepared and subjected to fractionation procedures by an HP-20 column chromatography and organic solvent extraction, as described below, to determine respective fractions for the xanthine oxidase inhibition activity.

(Extraction and Purification of Banaba Leaves)

Figure 2:
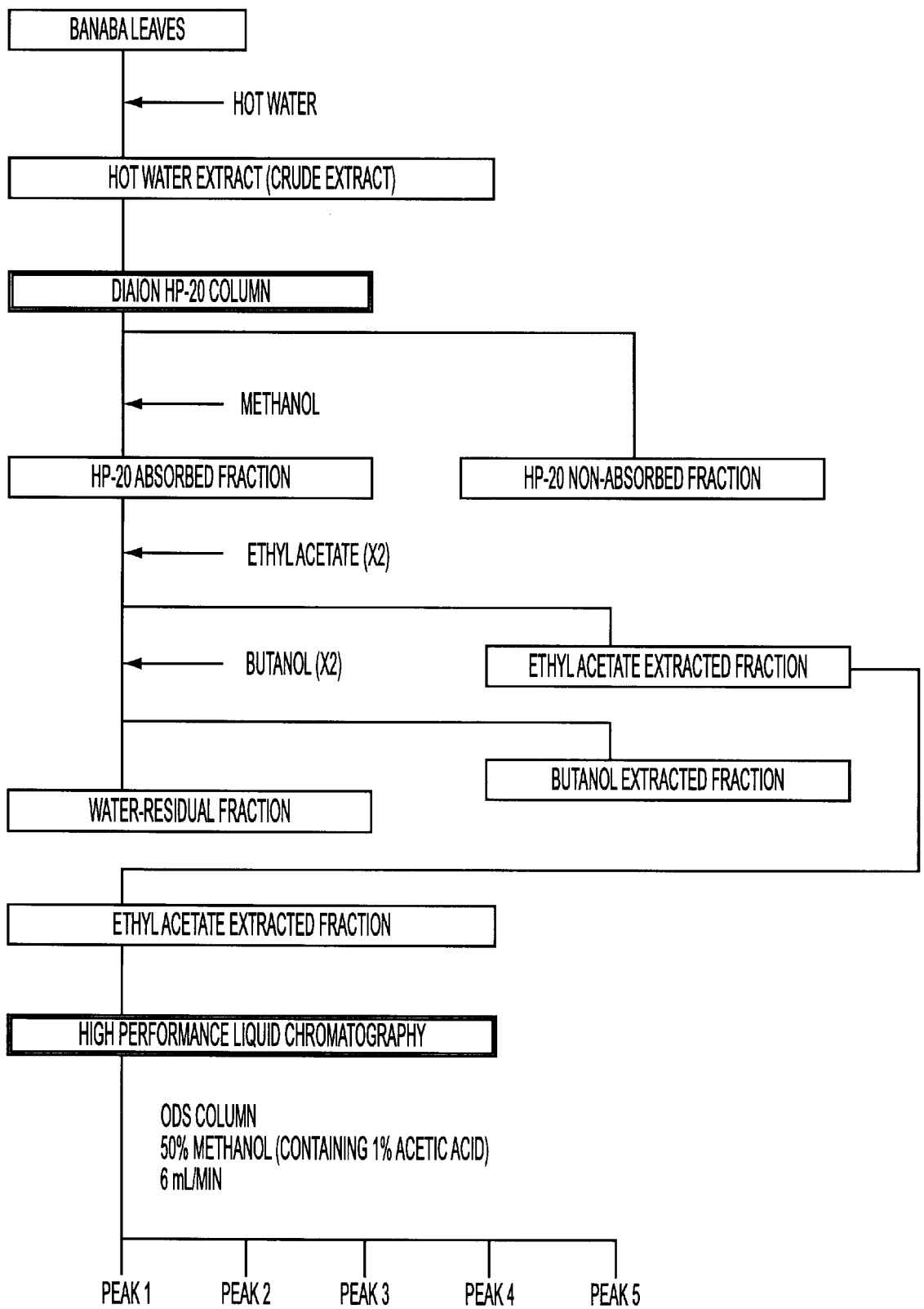
FIG. 2 is a diagram showing an example of extraction and purification steps of *Lagerstroemia speciosa* (banaba).

Banaba leaves were extracted and purified by the steps indicated in FIG. 2. Each fraction was determined for the xanthine oxidase inhibition activity according to the measurement method described below.

An appropriate amount of raw banaba leaves harvested in the Philippines was forced to dry sufficiently, and 1 kg of ground and well-mixed banaba leaves was extracted with 50 l of water at temperatures 95 to 100° C. for 30 minutes. The extracted solution thus obtained had a brix of about 1.5 percent. The resulting extracted solution was filtered, centrifuged, and then concentrated by an evaporator, followed by spray drying to produce an "hot-water extract," that is, a crude extract.

Next, a glass column having a diameter of 10 cm and a length of 100 cm was packed with 2.5 l of styrene-divinyl benzene synthetic resin (Diaion HP-20, Mitsubishi Kasei Kogyo K.K.), and the packed resin was washed with methanol and then distilled water. Subsequently, the above-mentioned "hot-water extract" (the entire amount) was dissolved in 1 l of distilled water and applied to the glass column. Then, distilled water was applied at an amount corresponding to about six times the volume of the column to remove a fraction of substances not adsorbed on the styrene-divinyl benzene synthetic resin (hereinafter referred to an "HP-20 non-adsorbed fraction"), and after that, methanol at an amount corresponding to about five times the volume of the column was applied to elute a fraction of substances adsorbed on the styrene-divinyl benzene synthetic resin (hereinafter referred to an "HP-20 adsorbed fraction").

The "HP-20 non-adsorbed fraction" and "HP-20 adsorbed fraction" obtained in this way were concentrated and freeze dried to yield a dried material, respectively.

Next, 200 g of the resulting "HP-20 adsorbed fraction" was dissolved in 1.5 l of distilled water, to which 2 l of ethyl acetate was added and the mixture was sufficiently shaken in a separating funnel to collect an "ethyl acetate extracted fraction" as components soluble in ethyl acetate. This extraction procedure with ethyl acetate was repeated twice to obtain "ethyl acetate extracted fractions." The fractions were concentrated and freeze dried to yield a dried material.

In addition, 1.5 l of butanol was added to residual components in the distilled water remaining in the separating funnel and the mixture was sufficiently shaken to collect a butanol-extracted fraction. This extraction procedure with butanol was repeated twice to obtain "butanol extracted fractions." The fractions were concentrated and freeze dried to yield a dried material.

Figure 3:
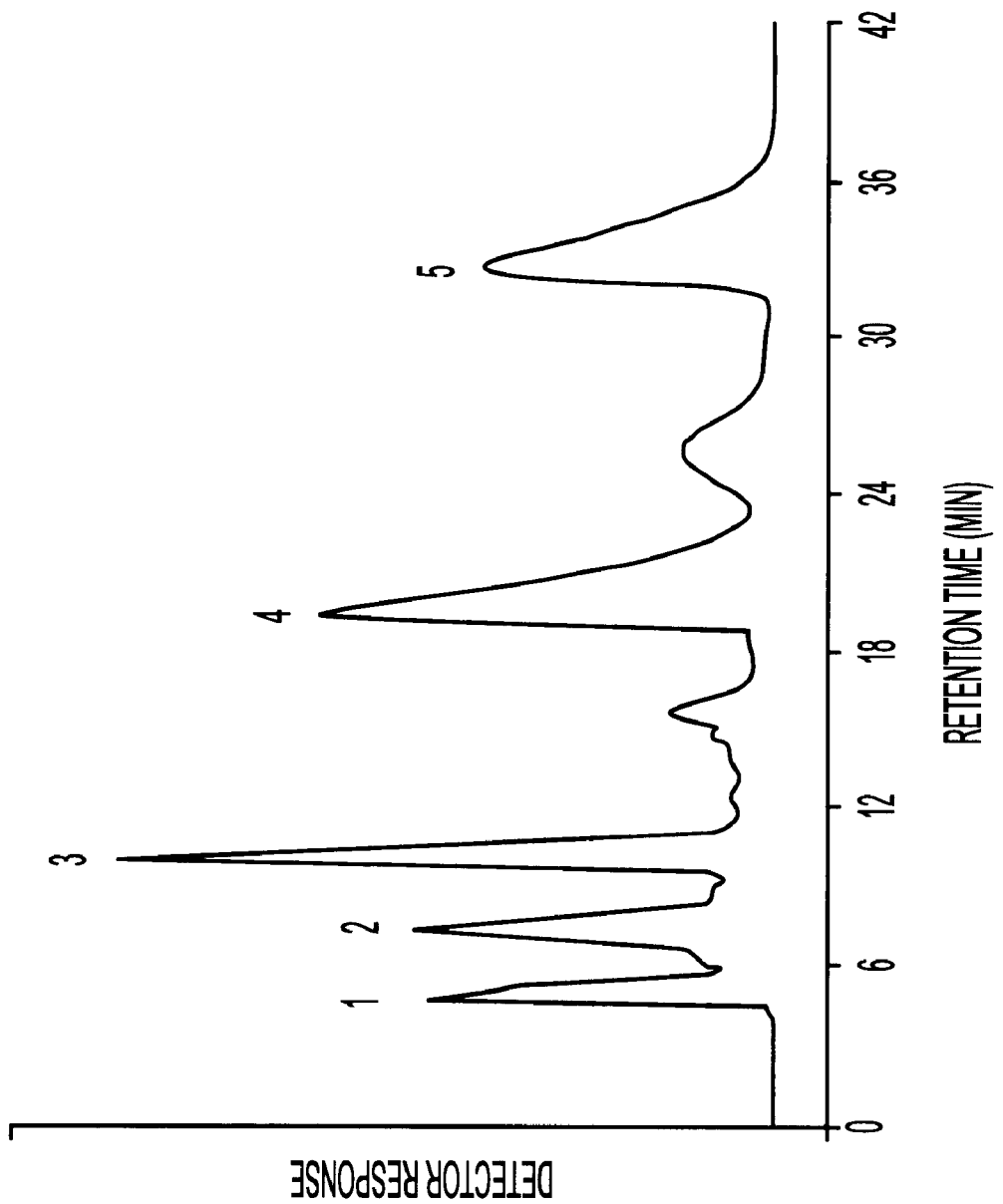
FIG. 3 is a graph showing the elution pattern of preparative high performance liquid chromatography.

With the "ethyl acetate extracted fraction" described above, a further purification procedure was carried out using a preparative high performance liquid chromatography. The used column was a YMC ODS 120A column (inner diameter 20 ml×250 ml), and 50 percent methanol (containing 1 percent acetic acid) was used at a flow rate of 6 ml/min under the room temperature. Eluting components were monitored by ultra violet absorption at 254 nm, and five major peaks were detected (FIG. 3). Each peak was collected with a fraction collector, and concentrated prior to freeze drying to yield a dried material (a "high performance liquid chromatography prepared component").

The "hot-water extract," "HP-20 non-adsorbed fraction," "HP-20 adsorbed fraction," "ethyl acetate extracted fraction," "butanol extracted fraction," and "high performance liquid chromatography prepared components" obtained in the above-mentioned steps were subjected to determination and comparison of the xanthine oxidase inhibition activity according to the measurement method described below.

Figure 4:
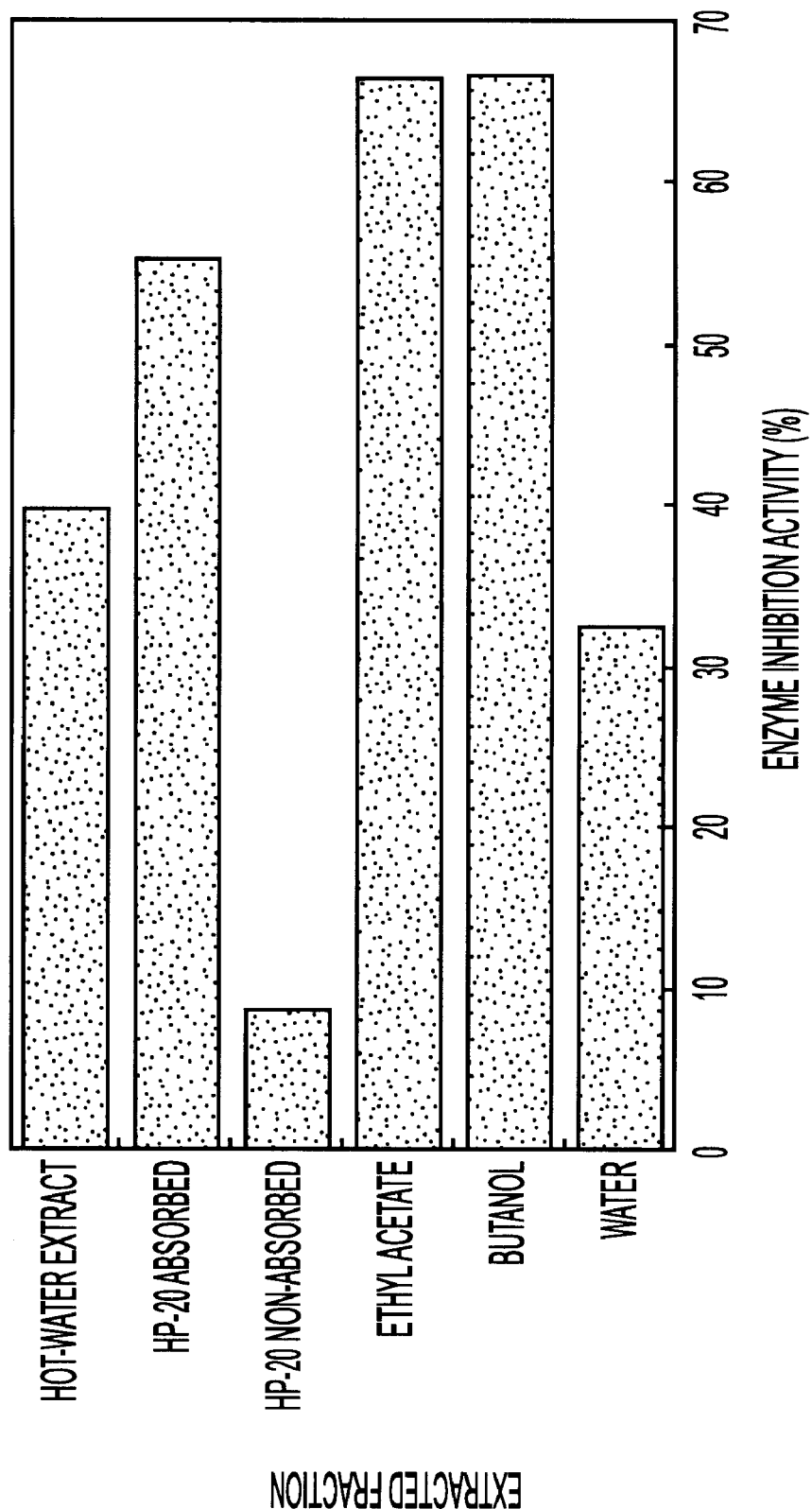
FIG. 4 is a graph showing the comparison of the xanthine oxidase inhibition activity of a hot-water extract, an HP-20 adsorbed fraction, an HP-20 non-adsorbed fraction, fractions by partition of the HP-20 adsorbed fraction with ethyl acetate and butanol, and its aqueous residue of *Lagerstroemia speciosa* (banaba).

FIG. 4 shows the xanthine oxidase inhibition activity in the separation steps.

It reveals that the activity can be enhanced by adsorbing the crude extract on HP-20, and to a higher extent by carrying out the extraction process of the HP-20 adsorbed fraction with ethyl acetate or butanol, and that the ethyl acetate and butanol extracted components display a much higher activity.

Figure 5:
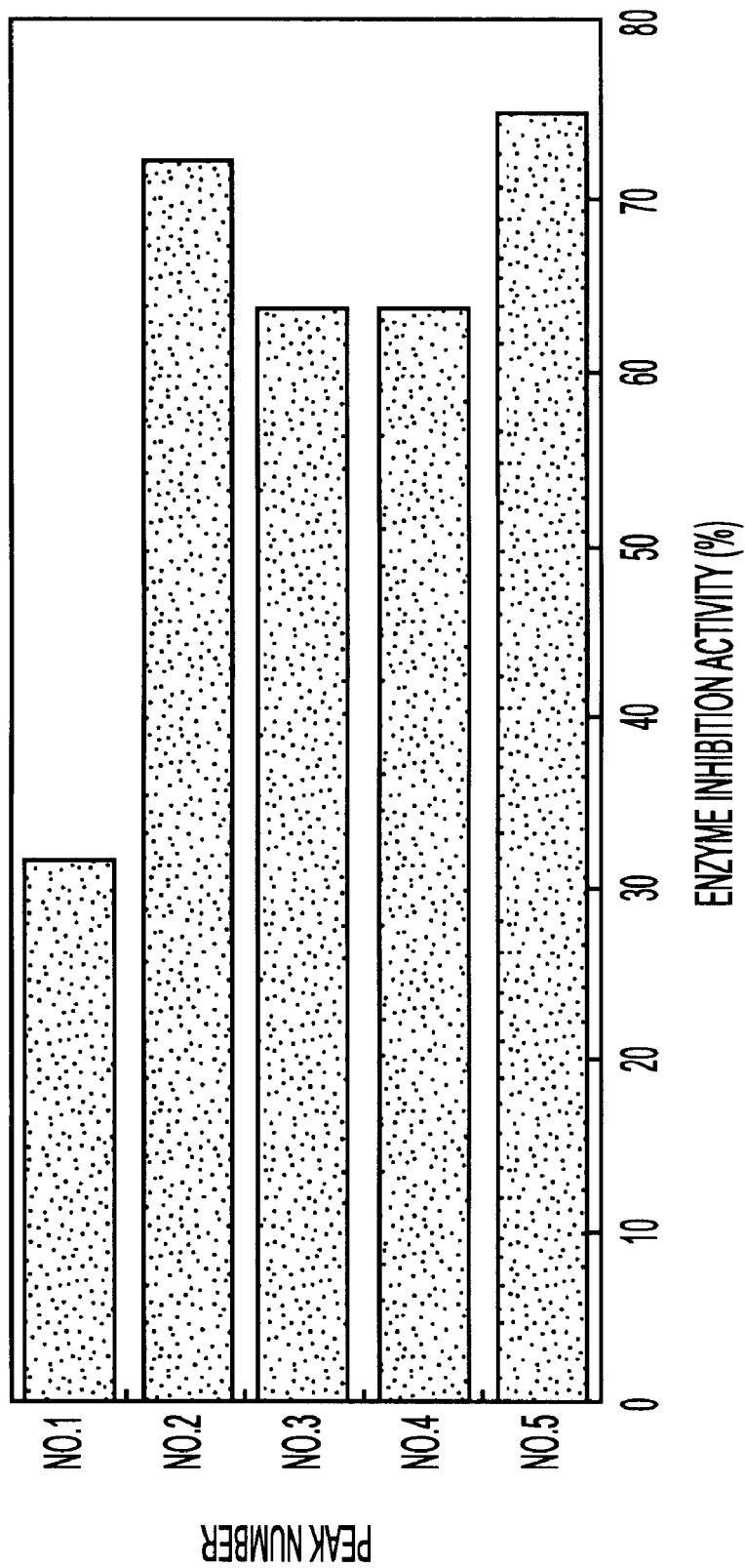
FIG. 5 is a graph showing the comparison of the xanthine oxidase inhibition activity of peak components obtained with preparative high performance liquid chromatography.

FIG. 5 shows the xanthine oxidase inhibition activity of the peaks obtained by purifying the ethyl acetate fraction with high performance liquid chromatography.

This indicates that the peaks other than Peak 1 had a higher inhibition activity than that of the ethyl acetate fraction itself. Peak 2 having a particularly strong inhibition activity was subjected to instrumental analysis employing NMR and mass spectroscopy, and was identified as a mixture of a lignan, 2,5-bis(4-hydroxy-3,5-dimethoxyphenyl)-3,4-bis (hydroxymethyl)-(2,3,4,5)-tetrahydrofuran (chemical formula 1) and a derivative of ellagic acid, valoneic acid dilactone (chemical formula 2). Additionally, Peak 3 was identified as an analogue compound of ellagic acid, 3,4,8,9,10-pentahydroxy-dibenzo[b,d]pyran-6-one (chemical formula 3), and Peak 4 as ellagic acid (chemical formula 4).

(Chemical formula 1)

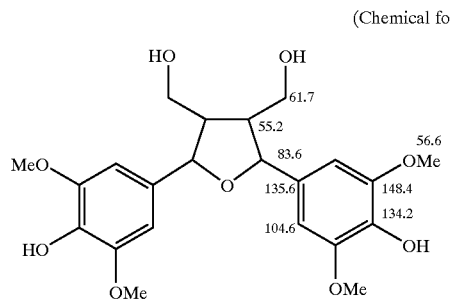

(Chemical formula 2)

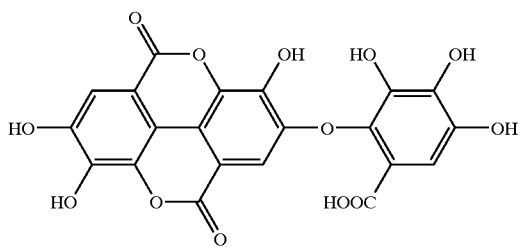

(Chemical formula 3)

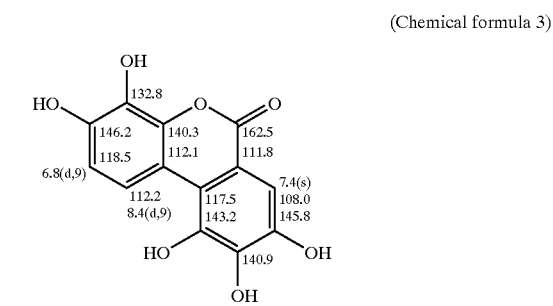

(Chemical formula 4)

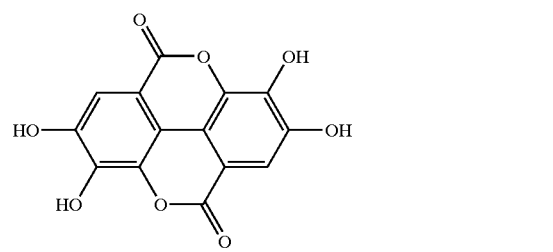

(Measurement of the Xanthine Oxidase Inhibition Activity)

Xanthine was used as the substrate, and the amount of uric acid produced by its oxidation enzyme, xanthine oxidase, was measured. All the reagents used were products from Wako Pure Chemical Industries, Ltd. In spectrophotometer cells were mixed beforehand 0.3 ml of 0.1 M phosphate buffer (pH 7.4), 0.02 ml or 0.1 ml of a sample solution, 0.18 ml or 0.1 ml of distilled water, and 0.1 ml of 0.12 U/ml xanthine oxidase, to which 0.1 mM xanthine was added to start the reaction. The uric acid produced was monitored for the absorbance at 295 nm. To the reference cell phosphate buffer was added, instead of xanthine oxidase. The xanthine oxidase inhibition activity was defined as 100 percent when no sample was added as control, and evaluated by the inhibition of the increase in absorbance resulting from the addition of the sample solutions.

What is claimed is:

1. A process for producing a xanthine oxidase inhibitor comprising:
   (a) extracting plant parts of *Lagerstroemia speciosa* with at least one member selected from the group consisting of water, hot water, and an organic solvent to obtain an extract;
   (b) adsorbing the extract onto a resin, selected from the group consisting of a styrene-divinyl benzene synthetic resin and a dextran synthetic resin to obtain resin adsorbed components;

(c) partitioning the resin adsorbed components by washing away non-adsorbed components with water and then eluting with ethyl acetate to obtain a fraction of ethyl acetate soluble components;

(d) purifying and isolating the fraction of ethyl acetate soluble components by high performance liquid chromatography to obtain high performance liquid chromatography separated components as determined by peaks of separation; and (e) recovering a substance from a second peak obtained from the high performance liquid chromatography as an xanthine oxidase inhibitor.

2. A process for producing a xanthine oxidase inhibitor comprising:

(a) extracting plant parts of *Lagerstroemia speciosa* with at least one member selected from the group consisting of water, hot water, and an organic solvent to obtain an extract;

(b) adsorbing the extract onto a resin, selected from the group consisting of a styrene-divinyl benzene synthetic resin and a dextran synthetic resin to obtain resin adsorbed components;

(c) partitioning the resin adsorbed components by washing away non-adsorbed components with water and then eluting with ethyl acetate to obtain a fraction of ethyl acetate soluble components;

(d) purifying and isolating the fraction of ethyl acetate soluble components by high performance liquid chromatography to obtain high performance liquid chromatography separated components as determined by peaks of separation; and (e) recovering a substance from a third peak obtained from the high performance liquid chromatography as an xanthine oxidase inhibitor.

3. A process for producing a xanthine oxidase inhibitor comprising:

(a) extracting plant parts of *Lagerstroemia speciosa* with at least one member selected from the group consisting of water, hot water, and an organic solvent to obtain an extract;

(b) adsorbing the extract onto a resin, selected from the group consisting of a styrene-divinyl benzene synthetic resin and a dextran synthetic resin to obtain resin adsorbed components;

(c) partitioning the resin adsorbed components by washing away non-adsorbed components with water and then eluting with ethyl acetate to obtain a fraction of ethyl acetate soluble components;

(d) purifying and isolating the fraction of ethyl acetate soluble components by high performance liquid chromatography to obtain high performance liquid chromatography separated components as determined by peaks of separation; and (e) recovering a substance from a fourth peak obtained from the high performance liquid chromatography as an xanthine oxidase inhibitor.

4. A method of inhibiting xanthine oxidase comprising administering a xanthine oxidase inhibitor obtained by the process of claim 1 to a subject in need of such inhibition.

5. A method of inhibiting xanthine oxidase comprising administering a xanthine oxidase inhibitor obtained by the process of claim 2 to a subject in need of such inhibition.

6. A method of inhibiting xanthine oxidase comprising administering a xanthine oxidase inhibitor obtained by the process of claim 3 to a subject in need of such inhibition.

7. A method of inhibiting xanthine oxidase comprising administering a xanthine oxidase inhibitor obtained by the process of claim 1 to a subject in need of such inhibition and wherein the obtained inhibitor comprises 2,5-bis-(4-hydroxy-3,5-dimethoxyphenyl)-3,4-bis-(hydroxymethyl)-(2,3,4,5)-tetrahydrofuran having the following chemical formula 1 and valoneic acid dilactone having the following chemical formula 2:

(Chemical formula 1)

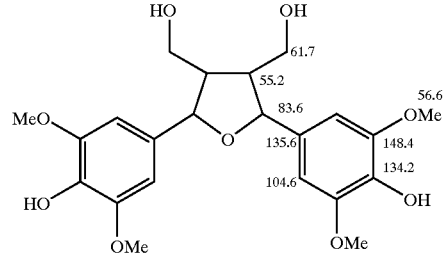

(Chemical formula 2)

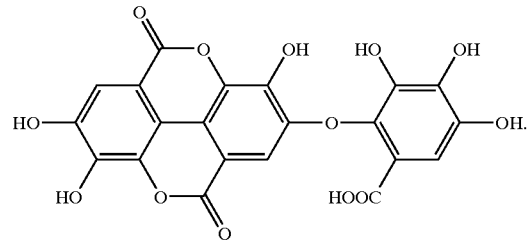

8. A method of inhibiting xanthine oxidase comprising administering a xanthine oxidase inhibitor obtained by the process of claim 2 to a subject in need of such inhibition and wherein the obtained inhibitor comprises 3,4,8,9,10-pentahydroxy-dibenzo[b,d]pyran-6-one having the following chemical formula 3:

(Chemical formula 3)

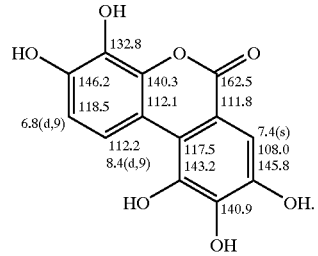

9. A method of inhibiting xanthine oxidase comprising administering a xanthine oxidase inhibitor obtained by the process of claim 3 to a subject in need of such inhibition and wherein the obtained inhibitor comprises ellagic acid having the following chemical formula 4:

(Chemical formula 4)

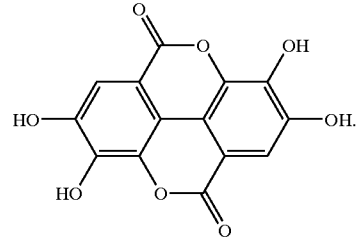

10. A product produced by the process of claim 1 wherein the obtained xanthine oxidase inhibitor comprises 2,5-bis-(4-hydroxy-3,5-dimethoxyphenyl)-3,4-bis-(hydroxymethyl)-(2,3,4,5)-tetrahydrofuran having the following chemical formula 1 and valoneic acid dilactone having the following chemical formula 2:

(Chemical formula 1)

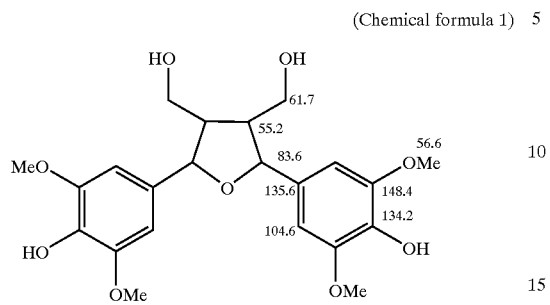

(Chemical formula 2)

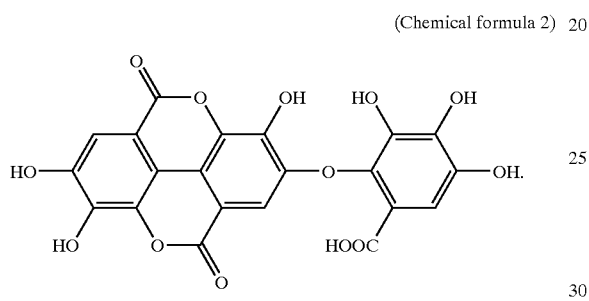

11. A product produced by the process of claim 2, wherein the obtained xanthine oxidase inhibitor comprises 3,4,8,9,10-pentahydroxy-dibenzo[b,d]pyran-6-one having the following chemical formula 3:

(Chemical formula 3)

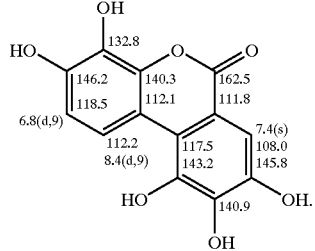

12. A product produced by the process of claim 3 wherein the obtained xanthine oxidase inhibitor comprises ellagic acid having the following chemical formula 4:

(Chemical formula 4)

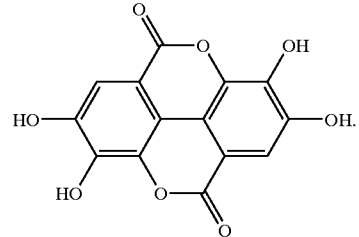

13. A xanthine oxidase inhibitor, produced by the process of claim 1.

14. A xanthine oxidase inhibitor, produced by the process of claim 2.

15. A xanthine oxidase inhibitor, produced by the process of claim 3.

* * * * *